United States Patent [19]
Stork

[11] Patent Number: 6,077,985
[45] Date of Patent: Jun. 20, 2000

[54] INTEGRATED DEETHANIZER/ETHYLENE FRACTIONATION COLUMN

[75] Inventor: Karl Stork, Houston, Tex.

[73] Assignee: Kellogg Brown & Root, Inc., Houston, Tex.

[21] Appl. No.: 09/266,214

[22] Filed: Mar. 10, 1999

[51] Int. Cl.$^7$ .................................. C07C 7/00; B01D 3/14
[52] U.S. Cl. .......................... 585/800; 203/99; 196/111; 202/158
[58] Field of Search ........................... 196/111; 202/158; 585/800; 203/99

[56] References Cited

U.S. PATENT DOCUMENTS

| | | | |
|---|---|---|---|
| 3,314,879 | 4/1967 | Lacy et al. ............................... | 208/356 |
| 3,412,016 | 11/1968 | Graven .................................... | 208/354 |
| 4,230,533 | 10/1980 | Giroux ...................................... | 203/1 |
| 5,339,648 | 8/1994 | Lackett et al. ........................... | 202/158 |
| 5,709,780 | 1/1998 | Ognisty et al. .......................... | 202/158 |
| 5,755,933 | 5/1998 | Ognisty et al. .......................... | 202/158 |

Primary Examiner—Walter D. Griffin
Attorney, Agent, or Firm—Kellogg Brown & Root, Inc.

[57] ABSTRACT

An integrated deethanizer and ethylene fractionation column and process for separating a feed stream comprising ethylene, ethane and $C_{3+}$ is disclosed. A single shell houses a refluxed upper portion and a lower portion of the column. A generally vertical wall partitions the lower portion of the column into a deethanizer section and an ethylene stripper section. The upper column portion is used as the absorption section of the ethylene fractionator. The feed is supplied to an intermediate stage in the deethanizer, and the deethanizer is operated at a lower pressure (and correspondingly lower temperature) matching that of the ethylene fractionation. The design allows the use of one slightly larger column in place of the two large columns previously used for separate deethanization and ethylene fractionation.

18 Claims, 6 Drawing Sheets

Front End Depropanizer Process Chilling and Demethanizer

INTEGRATED DEETHANIZER/ETHYLENE FRACTIONATION COLUMN

FIELD OF THE INVENTION

The present invention relates to an apparatus and method for the deethanization and ethylene fractionation in an olefin plant processing propane and heavier feedstocks, and particularly to the use of an integrated column which combines both the deethanizer and ethylene fractionator into a single column.

BACKGROUND OF THE INVENTION

A typical process for the separation and recovery of olefins from pyrolysis furnaces operated with feedstocks heavier than ethane, is known as the front end depropanizer and front end acetylene hydrogenation scheme. A brief review of the typical front end depropanizer process is in order.

Figure 1:
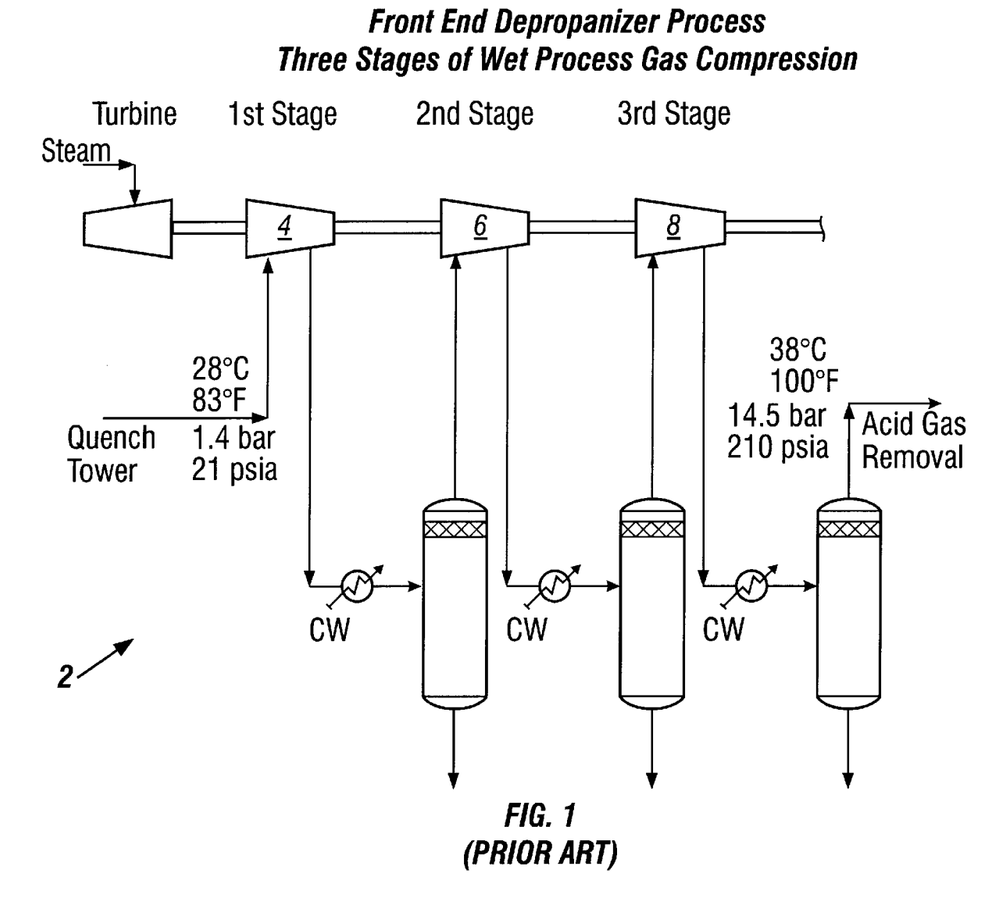
FIG. 1 (prior art) is a simplified process flow diagram showing the three stages of wet process gas compression in a front end depropanizer process.

Starting with the separation section 2 after the water quench, as shown on the simplified process flow diagram of FIG. 1, there are three stages 4,6,8 of conventional compression to raise the pressure of the process gas from just above atmospheric to a pressure of about 15 bars (210 psia). Condensed liquids, i.e. hydrocarbons and water, are separated.

Figure 2:
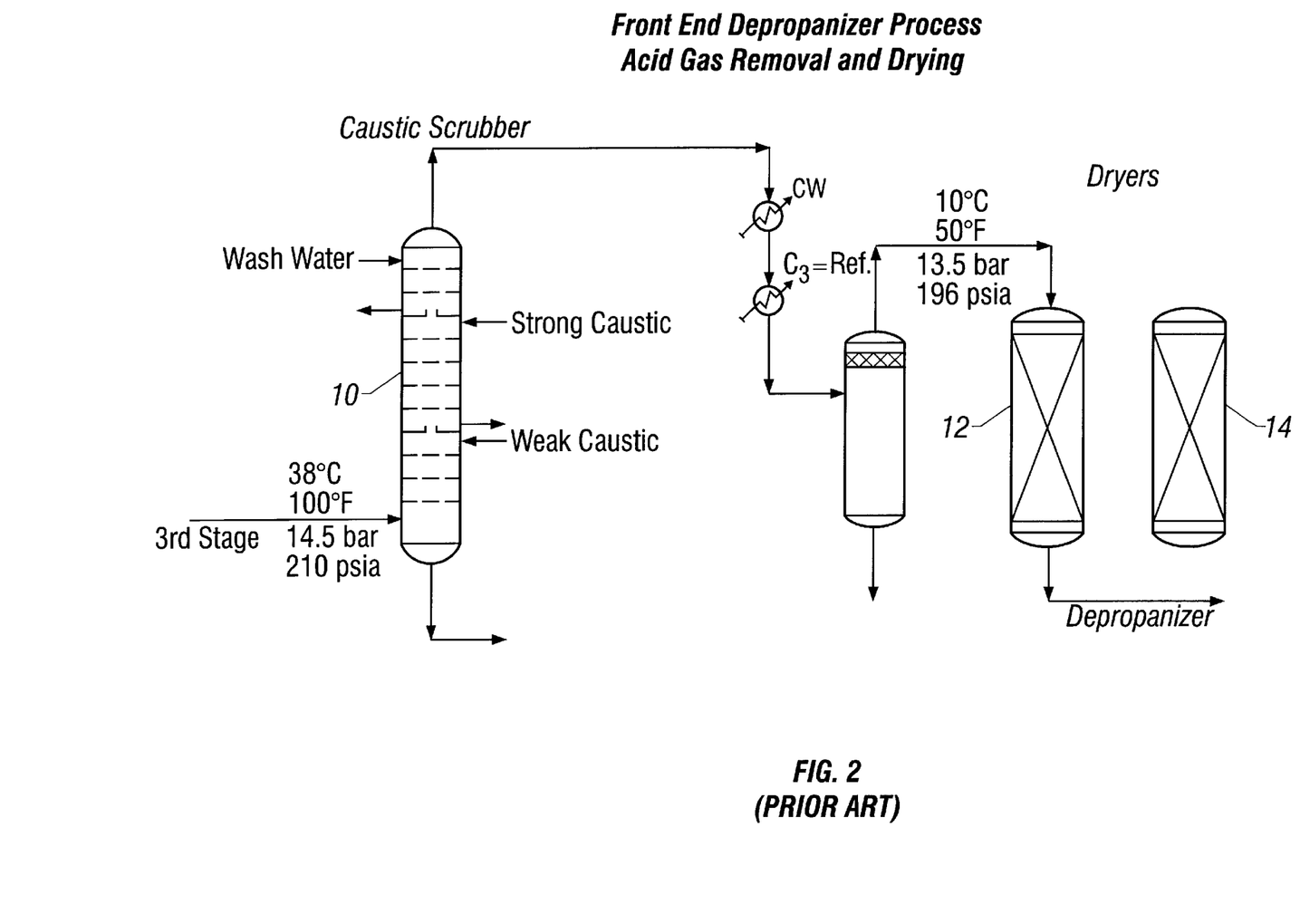
FIG. 2 (prior art) is a simplified flow diagram of acid gas removal and drying in a front end depropanizer process.

The gas is then treated in a conventional two or three stage caustic wash tower 10 as shown in FIG. 2 for the removal of carbon dioxide and hydrogen sulfide. The gas is cooled and mildly chilled before entering the dryers 12,14. Water is removed completely.

Figure 3:
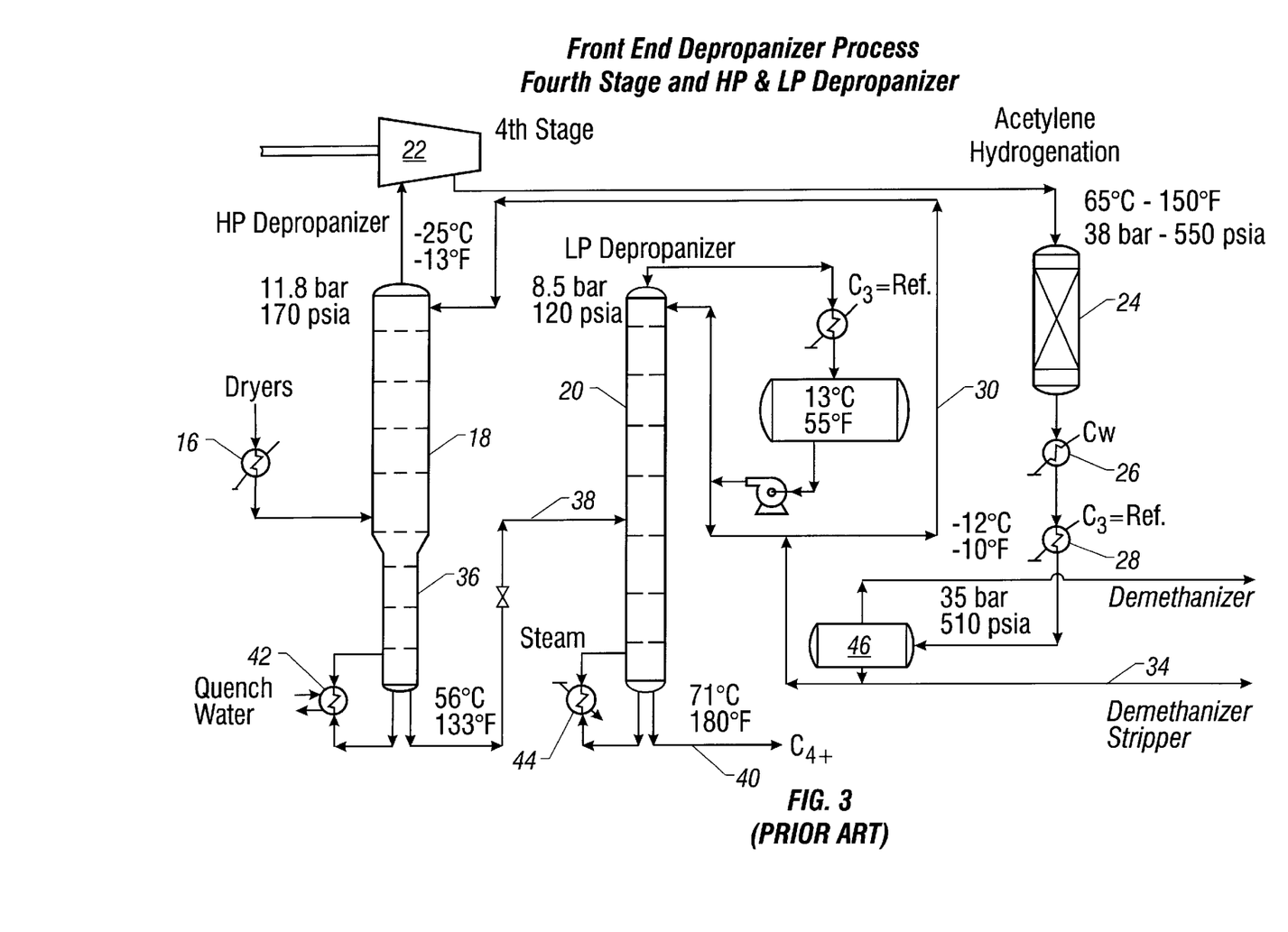
FIG. 3 (prior art) is a simplified process flow diagram of fourth stage compression and high pressure/low pressure depropanizers in a front end depropanizer process.

The gas is then further chilled in propylene refrigerant exchanger 16 seen in FIG. 3, and enters the high pressure depropanizer 18 which does not really operate at high pressure but is only called that because there is also a low pressure depropanizer 20. The high pressure depropanizer 18 typically operates at a pressure of 12 bars (170 psia), and the low pressure depropanizer 20 at a pressure of 8.5 bars (120 psia).

The overhead of the high pressure depropanizer 18 is usually compressed in compressor 22 to a pressure of 38 bars (550 psia) and is then sent to the acetylene hydrogenation system 24 which typically consists of two or three adiabatic reactors in series with inter-cooler for the removal of the heat of reaction. The reactor effluent is cooled in cooling water exchanger 26 and partially condensed in propylene refrigerant exchanger 28. A portion of the condensate is used as reflux via line 30 for the high pressure depropanizer 18. The rest is sent to the demethanizer stripper 32 (see FIG. 4) via line 34.

In the stripping section 36 of the high pressure depropanizer 18 only ethane and lighter components are removed, resulting in a fairly low bottoms temperature of 56° C. (133° F.). The bottoms product is sent via line 38 to the low pressure depropanizer 20 where it is separated into $C_3$'s and $C_{4+}$. The $C_3$ is used as reflux in the high pressure depropanizer 18 via line 30, while the $C_{4+}$ is sent to the debutanizer (not shown) via line 40. Due to the low operating pressure, the bottoms temperatures in the depropanizers 18,20 are quite low, namely 56° C. (133° F.) and 71° C. (160° F.). Therefore, there is no fouling in either tower 18,20 or their respective reboilers 42,44.

The acetylene hydrogenation unit 24 is highly efficient and selective. The acetylene removal easily results in acetylene concentrations of less than 1 ppm in the final ethylene product while the ethylene gain amounts to 50% or more of the acetylene. Due to the high hydrogen content of the feed gas, no carbonaceous material is deposited on the catalyst. The catalyst needs no regeneration and thus the reactors 24 need no spares. Green oil formation is miniscule.

In the acetylene hydrogenation reactor 24 about 80% of the methyl-acetylene and 20% of the propadiene are converted to propylene. If the olefins plant produces polymer grade propylene the remaining $C_3H_4$ can be easily fractionated into the propane product; the high conversion of methyl-acetylene and propadiene in the acetylene hydrogenation reactors obviates the need for an additional separate $C_3H_4$ hydrogenation system.

The operational stability of the acetylene hydrogenation reactor 24 is enhanced by its location in the gross overhead loop of the depropanizer 18 and in the minimum flow recycle circuit of the fourth stage of compression 22. These factors reduce the acetylene concentration in the inlet to the reactor 24 and stabilize the flow rate irrespective of the furnace throughput.

Figure 4:
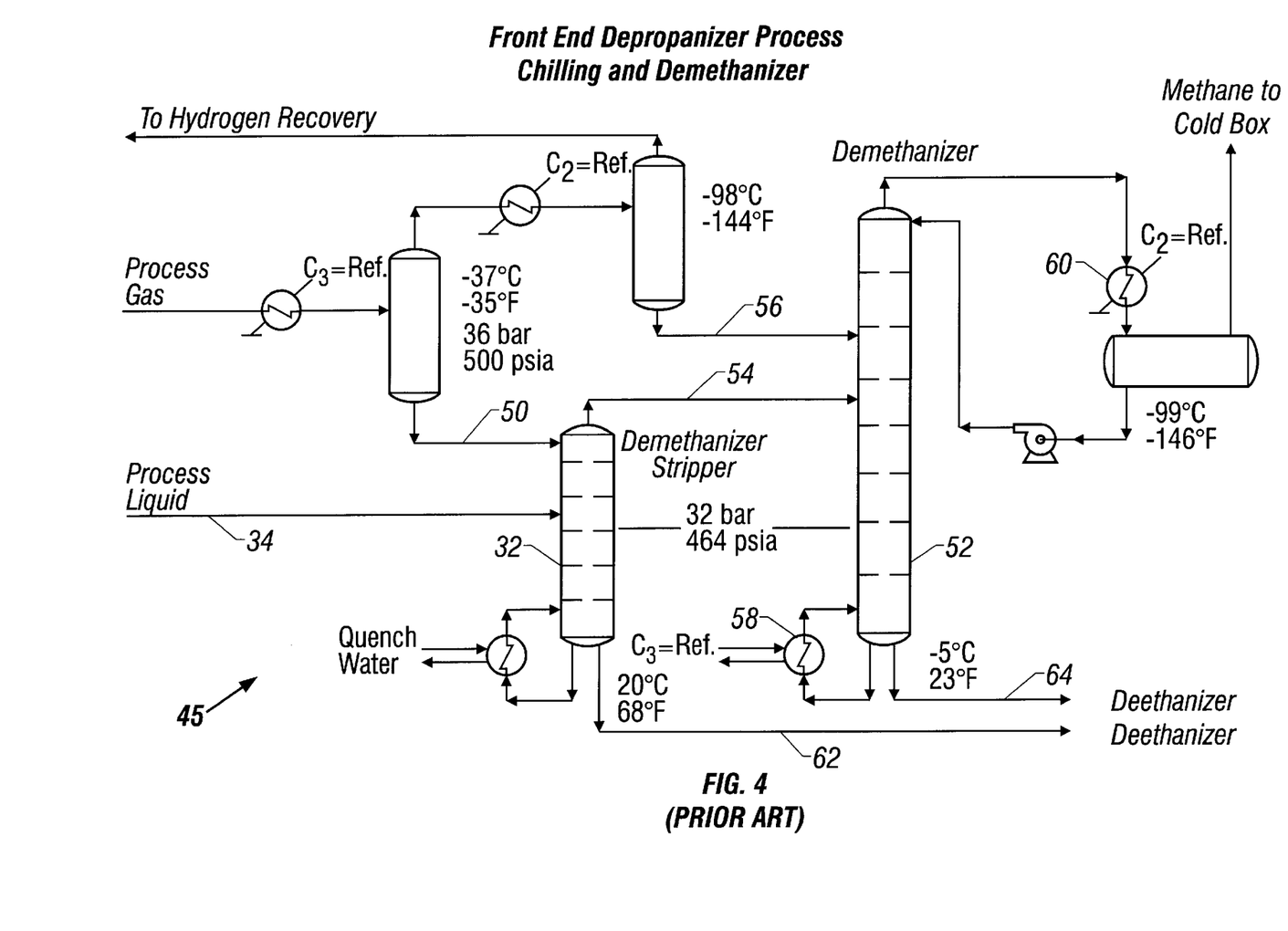
FIG. 4 (prior art) is a simplified process flow diagram of a demethanizer stripper and demethanizer in a front end depropanizer process.

The vapor and liquid from the reflux accumulator 46 of the high pressure depropanizer 18 flow to the chilling and demethanization section 48 (see FIG. 4). The liquid plus the condensate formed at −37° C. (−35° F.) is sent via respective lines 34 and 50 to the demethanizer stripper 32. The overhead vapor from the demethanizer stripper 32 plus the liquids formed at lower temperatures are sent to the main demethanizer 52 via respective lines 54 and 56. The tower 52 is reboiled by reboiler 58 with condensing propylene refrigerant, and reflux is condensed in heat exchanger 60 with low temperature ethylene refrigerant.

Figure 5:
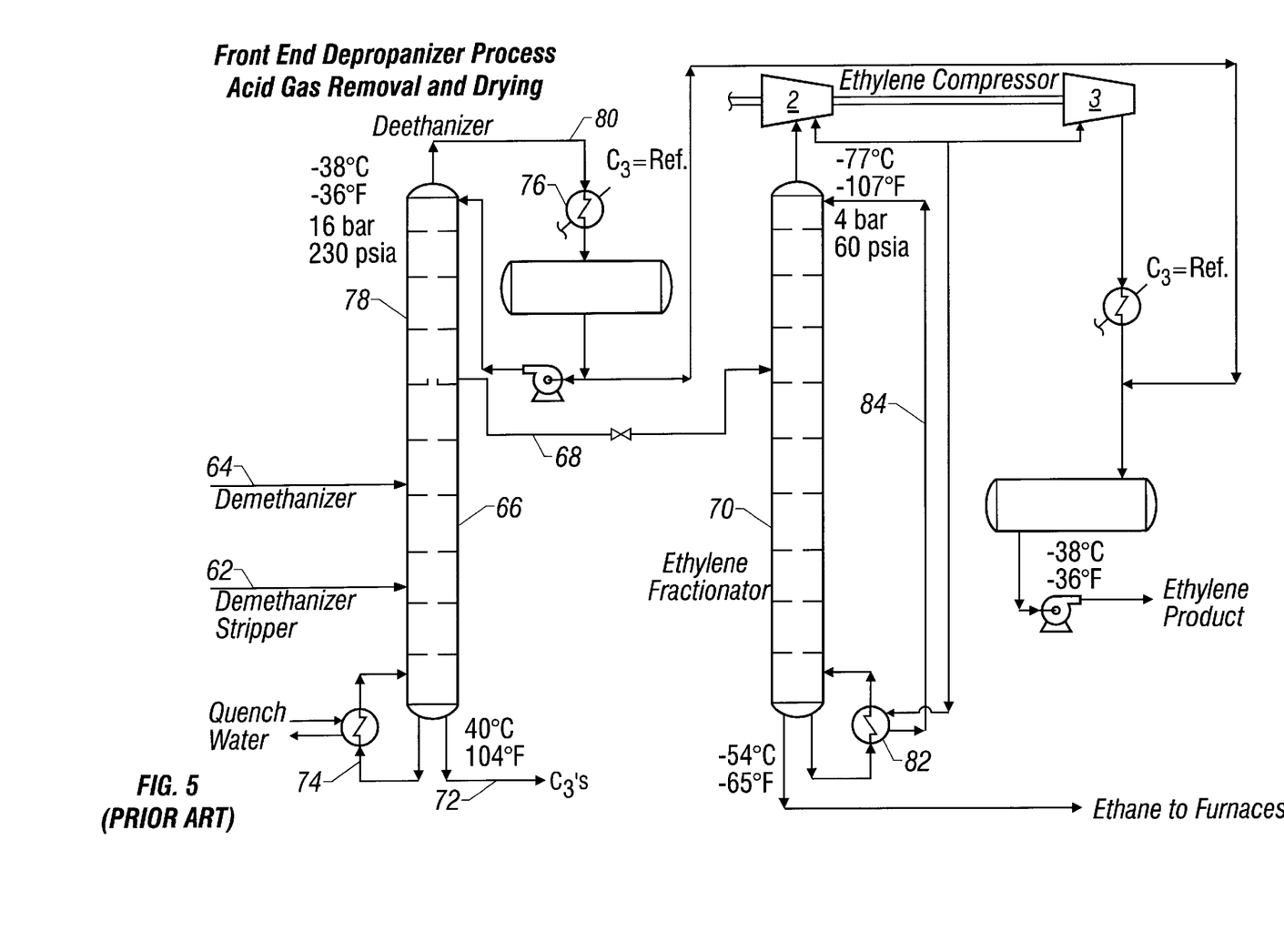
FIG. 5 (prior art) is a simplified flow diagram of the deethanizer and ethylene fractionator in a front e nd depropanizer process.

The respective bottoms products 62,64 of the two demethanizers 32,52, after some heat exchange which is not shown, enter the prior art deethanizer 66. The tower 66 recovers approximately 40 percent of the ethylene contained in the two feeds as high purity product. Sixty percent of the ethylene and all the ethane leave the tower 66 as a side stream 68 and proceed to the low pressure ethylene fractionator 70. The deethanizer 66 is reboiled by reboiler 74 with quench water and reflux is condensed in exchanger 76 with −40° propylene refrigerant. The bottoms product 72 of the deethanizer 66 is a stream containing propylene, propane and the remaining $C_3H_4$. It flows to a conventional propylene fractionator (not shown). Because of the ethylene fractionation in its top section 78, the deethanizer 66 has fifty more trays than a conventional deethanizer (without the side draw) which produces a mixed ethylene and ethane overhead product in line 80.

The ethylene fractionator 70 is a relatively low pressure tower typically operating at 4 bars (60 psia) with approximately 100 trays. It uses an open heat pump. Ethylene refrigerant is condensed in the reboiler 82 and is then used as reflux via line 84. Effectively, the reboiler 82 also serves as the reflux condenser. There are no reflux pumps and there is no reflux drum.

Other references of interest are U.S. Pat. Nos. 5,709,780 and 5,755,933, both to Ognisty et al.

SUMMARY OF THE INVENTION

The present invention combines the deethanizer and ethylene fractionator of the prior art into a single fractionation column, reduces the pressure of the deethanizer to that of the ethylene fractionator and locates the deethanizer and the stripping section of the ethylene fractionator in the bottom portion of a single distillation column divided by a vertical wall. Locating the deethanizer and the stripping sections of the ethylene fractionator in the bottom section of a single distillation column divided by a vertical wall has the capital cost savings of replacing two large columns with a slightly larger column; eliminates the deethanizer reflux condenser, drum and pumps; and employs a much smaller deethanizer reboiler.

In one aspect, the present invention provides an integrated deethanizer and ethylene fractionation column for separating a feed stream comprising ethylene, ethane and $C_{3+}$ into an ethylene stream, an ethane stream and a $C_{3+}$ stream. The integrated column is made of a single shell housing a refluxed upper portion and a lower portion. Each of the integrated column portions comprise multiple vapor-liquid contacting elements. A generally vertical wall partitions the lower portion into a deethanizer section and an ethylene stripper section. A feed line supplies at least one feed stream to at least one feed stage of the deethanizer section of the lower portion of the column, between a plurality of absorption stages above the feed stage and a plurality of stripping stages below the feed stage, for producing an overhead vapor stream from the deethanizer section consisting essentially of ethylene and ethane and a bottoms stream consisting essentially of $C_3$ and heavier components. A distribution pan with vapor chimney(s) at the lower end of the upper portion of the column facilitates passage of vapors from the deethanizer and ethylene stripper sections into the upper column portion, and collects liquid for passage from the upper portion of the column into the upper stage of the deethanizer section and into the ethylene stripping section.

The integrated column can have a deethanizer section comprising from 20 to 60 trays. The upper and lower portions of the integrated column preferably have the same cross-sectional diameter. The integrated column can also include a reboiler for the deethanizer section heated with high pressure depropanizer gross overhead or some other suitable heating medium. The integrated column can also include a reboiler for the ethylene stripper section, heated by ethylene condensed at a relatively higher pressure than the integrated column. The integrated column preferably includes a line for refluxing the upper portion of the column with the ethylene condensed in the ethylene stripper section reboiler. The integrated column can include a compressor for compressing overhead vapor from the upper portion of the column to the pressure of the ethylene stripper section reboiler. The integrated column preferably comprises respective liquid lines from the distribution pan to the tops of the dethanizer section and the ethylene stripper section. The line from the distribution pan to the top of the deethanizer section can include a valve for controlling the amount of liquid supplied to the deethanizer section. The integrated column preferably has an operating pressure of from 2 to 20 bars (30 to 290 psia).

In another aspect, the invention provides a process for separating a feed stream comprising ethylene, ethane and $C_{3+}$ into an ethylene stream, an ethane stream and a $C_{3+}$ stream. The method includes supplying the feed stream to the at least one feed stage of the deethanizer section of the lower portion of the integrated column described above; passing overhead vapor from the deethanizer and ethylene stripper sections through the chimney(s) of the distribution pan to the upper portion of the column; refluxing the upper portion of the column with ethylene and recovering essentially pure ethylene overhead from the upper portion of the column; passing liquid from the distribution pan into an upper stage of the deethanizer section and into an upper stage of the ethylene stripper section; reboiling the deethanizer section and recovering a $C_{3+}$ bottoms product stream therefrom essentially free of ethane and ethylene; and reboiling the ethylene stripper section and recovering an ethane bottoms product stream therefrom essentially free of ethylene and $C_{3+}$.

The deethanizer section preferably comprises from 20 to 60 trays, and the upper and lower portions of the integrated column have the same cross-sectional diameter. The process preferably includes feeding first and second feed streams from a demethanizer and a demethanizer stripper to different intermediate feed stages in the deethanizer section. The process can include controlling the amount of liquid feed to the upper stage of the deethanizer section from the distribution pan. The integrated column can be operated at a pressure from 2 to 20 bars (30 to 290 psia). The deethanizer section is preferably reboiled with high pressure depropanizer gross overhead. The process can further include compressing the overhead ethylene and condensing a portion of the compressed ethylene to supply heat for the reboiling of the ethylene stripper section. The condensed ethylene from the reboiling can be used for the refluxing of the upper portion of the integrated column.

DETAILED DESCRIPTION OF THE INVENTION

Figure 6:
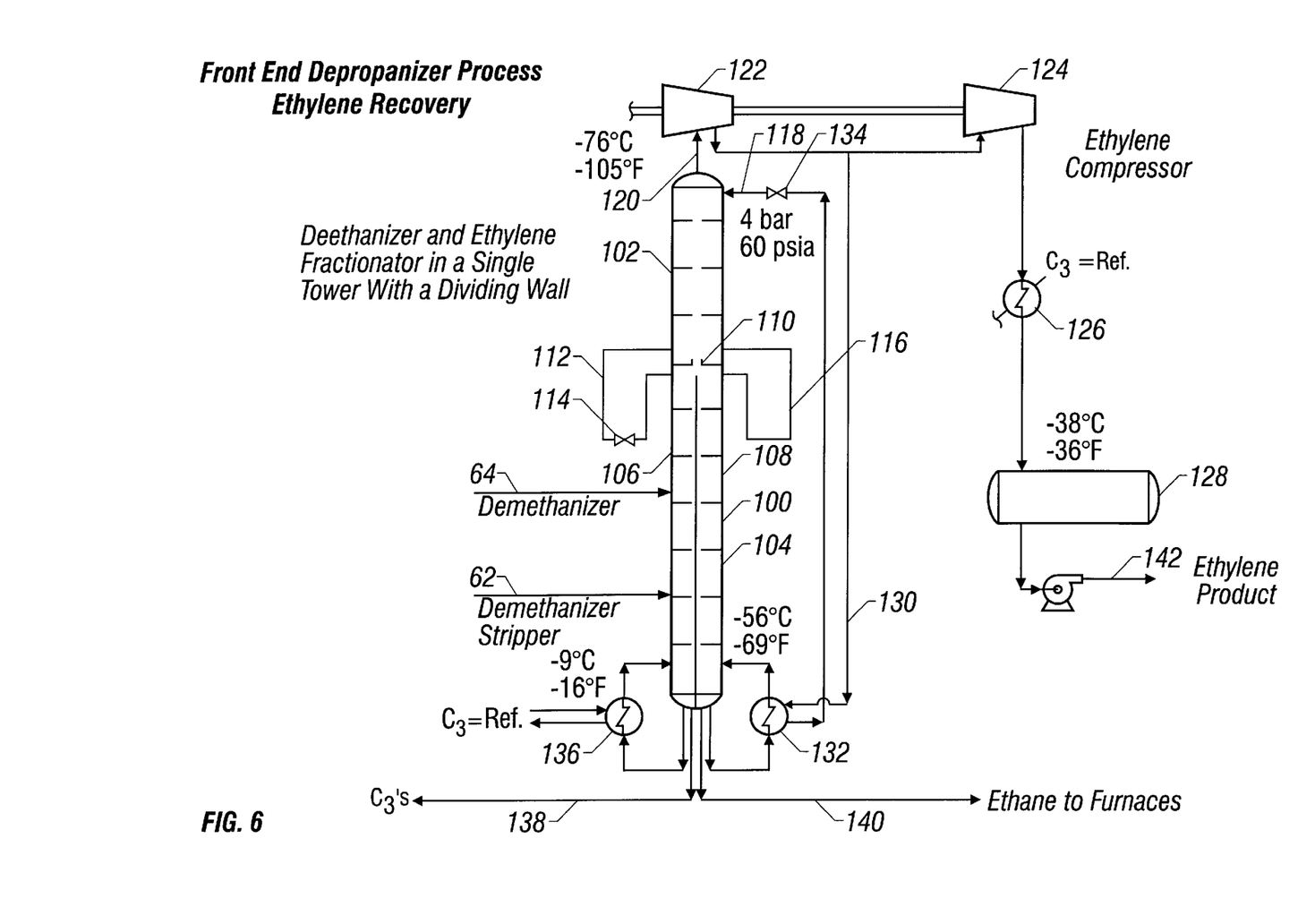
FIG. 6 is a simplified process flow diagram of ethylene recovery in a front end depropanizer process according to one embodiment of the present invention.

With reference to FIG. 6, a single tower 100 achieves the sharp separation of high purity ethylene as an overhead product, a mixed $C_{3+}$ product with an extremely low ethane content as a bottoms product on the left side 106, and an ethane product on the right side 108 of the lower portion 104 of the column 100 for recycle to the pyrolysis furnaces (not shown). The column 100 is preferably operated at a pressure of from 2 to 20 bars (30 to 290 psia), more preferably at a pressure of from 2 to 6 bars (30 to 90 psia), and especially at about 4 bars (60 psia).

The column 100 includes an upper portion 102 and the lower portion 104. The upper portion 102 serves as the absorption section of the ethylene fractionator. The lower section 104 of the column is partitioned by a vertical partition which divides the lower portion 104 into left and right sides 106,108, respectively. The left side 106 serves as the deethanizer, whereas the right side 108 serves as the stripping section of the ethylene fractionator.

The demethanizer stripper bottoms 62 and demethanizer bottoms 64 are fed to trays or stages in the left section 106 which have about the same composition. Vapors from the left section 106 pass overhead with vapors from the right section 108 through a distribution pan 110 which allows vapor to pass upwardly therethrough, but restrains liquid from passing from the upper column portion 102 into the lower column portion 104. The vapor from the left section 106 can be in fluid communication with the vapor from the right section 108 at the top tray or stage of each section 106,108.

A line 112 introduces liquid from the distribution pan 110 to the top stage of the left section 106. The line 112 can include a control valve 114 for controlling the rate of liquid reflux to the left section 106. A line 116 is used to introduce liquid from the distribution pan 110 to the top of right section 108. Typically the amount of reflux in line 112 is controlled via valve 114, while the line 116 is a liquid overflow from the distribution pan 110. The amount of liquid in line 112 is usually a fraction of the liquid in line 116.

The upper portion 102 of the column 100 is refluxed with ethylene via line 118. Essentially pure ethylene vapor is recovered overhead in line 120. The overhead ethylene vapor is compressed in compressors 122 and 124, cooled with propylene refrigerant in exchanger 126 and collected in accumulator 128. A portion of the compressed ethylene is supplied via line 130 to reboiler 132 which supplies heat to a lower end of the right section 108. The reboiler 132 can be external or internally located in the bottom of the right section 108. Ethylene vapor condensed in the reboiler 132 is let down across valve 134 into line 118 for reflux of the upper column portion 102 as described above.

The left section 106 is heated by reboiler 136 which cools propylene refrigerant to supply the necessary heat. A $C_{3+}$ product stream is obtained from the bottom of the left section 106 in line 138. An ethane product is obtained from the bottom of the right section 108 in line 140 and can be recycled to the pyrolysis furnace (not shown). The ethylene product is recovered via line 142.

EXAMPLE 1

As one example of the invention, the column 102 is designed for an ethylene plant producing 600 kt/a of ethylene and compared to the separate deethanizer/fractionator of the prior art. The conventional deethanizer has a diameter of 3.2 m, a height of 65.6 m, operates at 1.8 MPa, and uses 101 trays. The conventional fractionator has a diameter of 3.5 m, a height of 62.7 m, operates at a pressure of 0.95 MPa and uses 104 trays. In using the integrated column 100 of the present invention, the integrated column has a diameter of 4.0 m, a height of 67.0 m, operates at a pressure of 0.95 MPa and uses 106 trays. Approximately 70 trays are used in the upper column portion 102. The demethanizer bottoms feed stream 64 is supplied to tray 77, while the demethanizer stripper bottoms stream 62 is supplied to tray 83.

In the prior art deeethanizer, the overhead temperature is −38° C. (−36° F.) and the bottoms temperature is 40° C. (104° F.). In the conventional ethylene fractionator, the overhead temperature is −77° C. (−107° F.), while the bottoms temperature is −54° C. (−65° F.). With the integration of the deethanizer and ethylene fractionator into the single column 100 according to the present invention, the column 100 is operated with an overhead temperature of −76° C. (−105° F.). The bottom stage temperature in the deethanizer section 106 of the lower column portion 104 is reduced to −9° C. (16° F.) and is reboiled by heat exchange with the high pressure depropanizer 18 gross overhead. The duty of the ethylene fractionator reboiler 132 is 11.32 MW (8.94 MMBtu/hr), while the duty of the deethanizer reboiler 136 is reduced to just 2.62 MW (8.94 MMBtu/hr). The flow rates and compositions of the primary streams are presented in Table 1 below.

TABLE 1

| Stream Number | 64 | 62 | 138 | 112 |
|---|---|---|---|---|
| Ethylene (kmol/hr) | 1,676.0 | 869.9 | 0.0 | 853.5 |
| Ethane (kmol/hr) | 156.4 | 145.3 | 0.3 | 201.3 |
| Propyne (kmol/hr) | 0.1 | 0.9 | 1.0 | 0.0 |
| Propadiene (kmol/hr) | 0.9 | 8.0 | 8.9 | 0.0 |
| Propylene(kmol/hr) | 152.2 | 715.4 | 867.1 | 0.2 |
| Propane (kmol/hr) | 4.4 | 26.7 | 31.1 | 0.0 |
| Total (kmol/hr) | 1,990.0 | 1766.2 | 908.4 | 1055.0 |

| Stream Number | 140 | 116 | 118 | 120 | 142 |
|---|---|---|---|---|---|
| Ethylene (kmol/hr) | 0.9 | 2,917.4 | 4,666.3 | 7,211.3 | 2,545.0 |
| Ethane (kmol/hr) | 301.0 | 688.0 | 0.8 | 1.2 | 0.4 |
| Propyne (kmol/hr) | 0.0 | 0.0 | 0.0 | 0.0 | 0.0 |
| Propadiene (kmol/hr) | 0.0 | 0.0 | 0.0 | 0.0 | 0.0 |
| Propylene (kmol/hr) | 0.5 | 0.5 | 0.0 | 0.0 | 0.0 |
| Propane (kmol/hr) | 0.0 | 0.0 | 0.0 | 0.0 | 0.0 |
| Total (kmol/hr) | 302.4 | 3,605.9 | 4,667.1 | 7,212.5 | 2,545.4 |

A comparison of the construction costs indicates that the new system saves approximately US$5 million compared to the conventional system of FIGS. 1–5. This example also shows that the use of a single distillation tower for deethanization and ethylene fractionation has the advantages of using one tower instead of two large towers, elimination of the deethanizer reflux condenser, drum and pumps, and a much smaller deethanizer reboiler.

The invention is described above in illustrative terms which are not intended to limit the invention. Many variations will become apparent to those skilled in the art in view of the foregoing description. It is intended that all such variations within the scope and spirit of the appended claims be embraced thereby.

What is claimed is:

1. An integrated deethanizer and ethylene fractionation column for separating a feed stream comprising ethylene, ethane and $C_{3+}$ into an ethylene stream, an ethane stream and a $C_{3+}$ stream, comprising:

a single shell housing a refluxed upper portion and a lower portion, each of said portions comprising multiple vapor-liquid contacting elements;

a generally vertical wall partitioning the lower portion into a deethanizer section and an ethylene stripper section;

a feed line for supplying at least one feed stream to at least one feed stage of the deethanizer section of the lower portion of the column, between a plurality of absorption stages above the feed stage and a plurality of stripping stages below the feed stage, for producing an overhead vapor stream from the deethanizer section consisting essentially of ethylene and ethane and a bottoms stream consisting essentially of $C_3$ and heavier components;

a distribution pan at a lower end of the upper portion of the column for facilitating passage of vapors from the deethanizer and ethylene stripper sections into the upper column portion, and for dividing liquid for passage from the upper portion of the column into an upper stage of the deethanizer section and into the ethylene stripping section.

2. The integrated column of claim 1 wherein the deethanizer section comprises from 20 to 60 trays.

3. The integrated column of claim 1 wherein the upper and lower portions have the same cross-sectional diameter.

4. The integrated column of claim 1 including a reboiler for the deethanizer section heated with high pressure depropanizer gross overhead.

5. The integrated column of claim 1 including a reboiler for the ethylene stripper section heated by ethylene condensed at a relatively higher pressure than the integrated column.

6. The integrated column of claim 5 including a line for refluxing the upper portion of the column with the ethylene condensed in the ethylene stripper section reboiler.

7. The integrated column of claim 5 including a compressor for compressing overhead vapor from the upper portion of the column to the pressure of the ethylene stripper section reboiler.

8. The integrated column of claim 1 comprising respective liquid lines from the distribution pan to the tops of the deethanizer section and the ethylene stripper section.

9. The integrated column of claim 8 wherein the line from the distribution pan to the top of the deethanizer section includes a valve for controlling the amount of liquid supplied to the deethanizer section.

10. The integrated column of claim 1 having an operating pressure of from 2 to 20 bars (30 to 290 psia).

11. A process for separating a feed stream comprising ethylene, ethane and $C_{3+}$ into an ethylene stream, an ethane stream and a $C_{3+}$ stream, comprising:

supplying the feed stream to the at least one feed stage of the deethanizer section of the lower portion of the integrated column of claim 1;

passing overhead vapor from the deethanizer and ethylene stripper sections through the distribution pan to the upper portion of the column;

refluxing the upper portion of the column with ethylene and recovering essentially pure ethylene overhead from the upper portion of the column;

passing liquid from the distributor pan into an upper stage of the deethanizer section and into an upper stage of the ethylene stripper section;

reboiling the deethanizer section and recovering a $C_{3+}$ bottoms product stream therefrom essentially free of ethane and ethylene;

reboiling the ethylene stripper section and recovering an ethane bottoms product stream therefrom essentially free of ethylene and $C_{3+}$.

12. The process of claim 11 wherein the deethanizer section comprises from 20 to 60 trays and the upper and lower portions of the column have the same cross-sectional diameter.

13. The process of claim 11 wherein first and second feed streams from a demethanizer and a demethanizer stripper are fed to different intermediate feed stages in the deethanizer section.

14. The process of claim 11 including controlling the amount of liquid feed to the upper stage of the deethanizer section from the distribution pan.

15. The process of claim 11 wherein the integrated column is operated at a pressure from 2 to 20 bars (30 to 290 psia).

16. The process of claim 11 wherein the deethanizer section is reboiled with high pressure depropanizer gross overhead.

17. The process of claim 11 further comprising compressing the overhead ethylene and condensing a portion of the compressed ethylene to supply heat for the reboiling of the ethylene stripper section.

18. The process of claim 17 wherein the condensed ethylene from the reboiling is used for the refluxing of the upper portion of the integrated column.

* * * * *